United States Patent [19]  
Drake

[11] 4,440,950  
[45] Apr. 3, 1984

[54] PROCESS FOR PREPARATION OF AMINOBENZALDEHYDES AND AMINOBENZYLKETONES

[75] Inventor: Charles A. Drake, Bartlesville, Okla.

[73] Assignee: Phillips Petroleum Company, Bartlesville, Okla.

[21] Appl. No.: 441,584

[22] Filed: Nov. 15, 1982

[51] Int. Cl.³ .............................................. C07C 85/18
[52] U.S. Cl. ................................................... 564/305
[58] Field of Search ......................................... 564/305

[56] References Cited

U.S. PATENT DOCUMENTS 3,316,261  4/1967  Speranza et al. ............... 564/305 X
4,273,785  6/1981  Shepherd ......................... 564/305 X

FOREIGN PATENT DOCUMENTS 57927  8/1969  Poland ................................ 564/305

OTHER PUBLICATIONS

J. Chem. Soc., 1945, pp. 276–277, 1945.
Chem. Abs., 62, p. 7691g, (1965).

Primary Examiner—Paul F. Shaver

[57] ABSTRACT

An improved process for the formation of a dihydrocarbylaminobenzaldehyde or dihydrocarbylaminobenzylketone is provided consisting of (a) reacting a N,N-dihydrocarbylaniline and a protected Schiff's base in the presence of water, a carboxylic acid, and an ammonium salt of a carboxylic acid followed by (b) hydrolyzing the resulting reactant product of (a).

7 Claims, No Drawings

PROCESS FOR PREPARATION OF AMINOBENZALDEHYDES AND AMINOBENZYLKETONES

This invention relates to an improved process for the synthesis of aminobenzaldehydes and aminobenzylketones.

It is known to one skilled in the art that a N,N-dialkylaminobenzaldehyde can be prepared by reacting a N,N-dialkylaniline and a protected Schiff's base such as hexamethylenetetramine in the presence of a carboxylic acid and water and then hydrolyzing the resulting reaction product. For example, Polish Pat. No. 57,927 discloses the production of p-dimethylaminobenzaldehyde by reaction of N,N-dimethylaniline with hexamethylenetetramine in the presence of water and acetic acid. The desired product, p-dimethylaminobenzaldehyde, is obtained in the amount of 73% of the theoretical yield after hydrolysis of the initially formed product.

Since aminobenzaldehydes and aminobenzylketones are useful for production of viscosity index improvers and N-containing polymers for blending with other polymers to improve impact resistance, a process which would give increased yield over that of the art would be highly desirable.

It is thus an object of this invention to provide a process for the production of aminobenzaldehydes and aminobenzylketones in improved yield.

Other aspects, objects, and advantages of the present invention will become apparent from the specification and the claims.

In accordance with the present invention I have discovered that increased yields of aminobenzaldehydes and aminobenzylketones are achieved by the addition of an ammonium salt of a carboxylic acid to the reaction. In particular, I have discovered that such increased yields are obtained by a process consisting of (a) reacting an N,N-dihydrocarbylaniline and a protected Schiff's base in the presence of a carboxylic acid, an ammonium salt of a carboxylic acid, and water followed by (b) hydrolyzing the resulting product of (a).

The aminobenzaldehydes and aminobenzylketones produced by the process of the present invention are defined by the formula

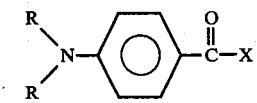

wherein each R is individually a $C_1$ to $C_{20}$ hydrocarbyl radical and X either is hydrogen or a $C_1$ to $C_{10}$ hydrocarbyl radical. Examples of these benzaldehydes include p-dimethylaminobenzaldehyde, p-diethylaminobenzaldehyde, and p-dihexylaminobenzaldehyde; examples of these benzylketones include p-dimethylaminobenzyl methyl ketone and p-dimethylaminobenzyl ethyl ketone.

N,N-dihydrocarbylanilines for use in this invention may be represented by the formula:

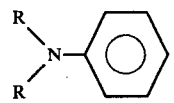

wherein R is as previously defined. Examples include N,N-dimethylaniline, N,N-diethylaniline, and N,N-dihexylaniline.

Protected Schiff's bases used in the present invention are stable products derived from the reaction of ammonia with a $C_1$ to $C_{10}$ aldehyde. In general, the reaction product of R'CHO with ammonia, where R' is $C_1$ to $C_9$ hydrocarbyl radical, is suitable. Most conveniently employed is hexamethylenetetramine, obtained by reaction of formaldehyde with ammonia.

Carboxylic acids useful in the present invention are defined by the formula R"COOH wherein R" is either H or a $C_1$ to $C_{10}$ hydrocarbyl radical. Examples of suitable carboxylic acids include formic acid, acetic acid, propionic acid, butyric acid and caproic acid.

Ammonium salts of carboxylic acids are presented by the formula:

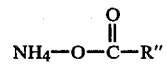

wherein R" is the same as previously defined. Examples of such salts include ammonium acetate and ammonium propionate. The ammonium salt employed will preferably be analogous to the carboxylic acid employed, e.g., where acetic acid is employed, ammonium acetate would be the preferred ammonium salt.

The process of the present invention employs the reagents in the following amounts based upon 1 mole of the N,N-dihydrocarbylaniline:

| Ingredient | Mole Ratio of Ingredient | |
|---|---|---|
| | Broad | Preferred |
| Protected Schiff's Base | .3–20 | 1–5 |
| Carboxylic Acid | 1–50 | 2–20 |
| $H_2O$ | 1–20 | 2–10 |
| Ammonium Salt | .1–10 | .2–4 |

The present invention can be carried out at a temperature broadly from about 100° C. to about 200° C., preferably about 115° C. to about 150° C. Reaction time can vary broadly from about 5 minutes to about 8 hours, preferably from about ½ to about 4 hours. Although reaction pressure has not been found to be critical, the reaction can be carried out from atmospheric up to about 2000 psig. Preferably the reaction will be carried out at autogeneous pressure, or from about 100 to about 500 psig.

The present invention can also be carried out in a continuous as well as batchwise manner.

The following examples illustrate the present invention.

EXAMPLE I

Control

N,N-dimethylaniline (DMA), hexamethylenetetramine (HMTA), acetic acid (HOAc) and water ($H_2O$) were all charged to a 1 liter stainless steel Magnedrive Autoclave Engineers stirred tank reactor. The autoclave was then flushed with a nitrogen purge, sealed with a 10–20 psig $N_2$ cap, and subsequently heated to 135° C. and maintained at that temperature and autogeneous pressure for about 1 hour. All runs and the particular molar quantity of reactant, based upon 1 mole of DMA are given below. Product yields were determined either by gas chromatographic analysis of the unhydrolyzed reaction product (employing cyclohexylbenzene as internal standard), or by acid hydrolysis of the Schiff's base product with 3 volumes of dilute acid per volume of reactor effluent followed by filtration to collect product.

| Run | Mole Ratio of Reagent[a] | | | DMA Conv, mol % | Sel. to DMAB, mol % | Yield of DMAB, mol % |
| --- | --- | --- | --- | --- | --- | --- |
| | HMTA | HOAc | H$_2$O | | | |
| 1 | 1.5 | 7.0 | 3.5 | 100 | 71 | 71 |
| 2 | 1.5 | 7.0 | 3 3 | 100 | 73 | 73 |
| 3 | 1.5 | 2.8 | 3.3 | 55 | 59 | 32 |
| 4 | 1.5 | 4.2 | 3.3 | 69 | 62 | 43 |
| 5 | 1.5 | 5.6 | 3.3 | 88 | 66 | 58 |
| 6 | 1.5 | 7.0 | 3.3 | 100 | 72 | 72 |

[a]Relative to 1 mole of DMA

The data indicate that using the conventional method a maximum yield of 73% of the desired product p-dimethylaminobenzaldehyde (DMAB) is obtained.

EXAMPLE II

Addition of Ammonium Acetate

Relative to 1 mole of DMA, 1.5 moles of HMTA, 7.0 moles of HOAc, and 3.3 moles of water were charged to an autoclave reactor as described in Example I. In addition, 0.4 mole of NH$_4$OAc were added. The reaction was carried out at a temperature of 135° C. for 1 hour.

Product analysis showed 100 mole percent conversion of the DMA as well as an 80 mole percent selectivity to the desired product p-dimethylaminobenzaldehyde (DMAB). Therefore, a yield of 80 mole percent of the DMAB was obtained.

This example demonstrates that the addition of ammonium acetate improves the yield of DMAB relative to the process employed when NH$_4$OAc is absent (80 mole percent vs. 73 mole percent). The addition of NH$_4$OAc maintains a complete conversion of the N,N-dimethylaniline as well as a high selectivity to DMAB.

Reasonable variations and modifications are possible from the foregoing without departing from the scope of this invention.

I claim:

1. A process for the production of an N,N-dihydrocarbylaminobenzyldehyde or N,N-dihydrocarbylaminobenzylketone of the formula

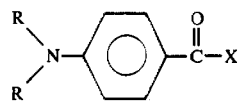

consisting of (a) reacting an N,N-dihydrocarbylaniline of the formula

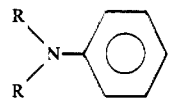

and a protected Schiff's base, derived from the reaction of ammonia and an aldehyde of the formula R'CHO, in the presence of a carboxylic acid of the formula R"COOH, an ammonium salt of a carboxylic acid of the formula

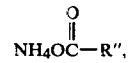

and water wherein R is a C$_1$ to C$_{20}$ hydrocarbyl radical, R' is either H or a C$_1$ to C$_9$ hydrocarbyl radical, X is either H or a C$_1$ to C$_{10}$ hydrocarbyl radical, and R" is either hydrogen or a C$_1$ to C$_{10}$ hydrocarbyl radical, followed by (b) hydrolysis of the resulting product of (a).

2. A process as in claim 2 wherein said protected Schiff's base is present in the range of 0.3–20 moles, said carboxylic acid is present in the range of 1–50 moles, said water is present in the range of 1–20 moles and said ammonium salt is present in the range of 0.1–10 moles per mole of said N,N-dihydrocarbylaniline.

3. A process according to claim 2 wherein said protected Schiff's base is present in the range of 1–5 moles, said carboxylic acid is present in the range of 2–20 moles, said water is present in the range of 2–10 moles, and said ammonium salt is present in the range of 0.2–4 moles per mole of said N,N-dihydrocarbylaniline.

4. A process according to claim 3 carried out at a temperature of from about 115° C. to about 150° C. for about 0.5 to about 4 hours.

5. A process according to claim 4 carried out at 135° C. for 1 hour.

6. A process according to claim 3 wherein R is CH$_3$ and R' is H.

7. A process according to claim 6 wherein R" is CH$_3$.

* * * * *